United States Patent [19]

Battista

[11] 4,393,042

[45] Jul. 12, 1983

[54] ULTRA HIGH-FOAM DENTIFRICE

[76] Inventor: Orlando A. Battista, 3725 Fox Hollow Rd., Fort Worth, Tex. 76109

[21] Appl. No.: 323,394

[22] Filed: Nov. 20, 1981

Related U.S. Application Data

[63] Continuation-in-part of Ser. No. 176,013, Aug. 7, 1980, abandoned.

[51] Int. Cl.$^3$ ............................................. A61K 9/16
[52] U.S. Cl. ................................................... 424/49
[58] Field of Search .................................. 424/49–58

[56] References Cited

U.S. PATENT DOCUMENTS

| | | | |
|---|---|---|---|
| 85,166 | 12/1868 | Colburn | 424/58 |
| 111,821 | 2/1871 | Danforth | 424/58 |
| 115,719 | 6/1871 | Draper | 424/58 |
| 1,379,744 | 5/1921 | Congreve | 424/49 |
| 1,633,336 | 6/1927 | Larson | 424/49 |
| 1,643,618 | 9/1927 | Bruck | 424/56 |
| 2,124,971 | 7/1938 | Eisenberg et al. | 424/49 |
| 2,995,521 | 8/1961 | Bluard | 424/49 |
| 3,692,894 | 9/1972 | Amo et al. | 424/56 |
| 4,206,198 | 6/1980 | Schmolka | 424/49 |
| 4,223,003 | 9/1980 | Scheller | 424/7 |
| 4,301,141 | 11/1981 | Scheller | 424/7 |

*Primary Examiner*—Shep K. Rose
*Attorney, Agent, or Firm*—George F. Mueller

[57] ABSTRACT

A dentifrice comprising a non-toxic soap and/or detergent without an unpleasant taste at concentrations from at least about 25 percent to about 50 percent and water at a minimum alkaline pH of 7.5 and capable of producing high viscosity bodied foams capable of physically capturing mouth bacteria and food particles, and allowing them to be flushed away with the foam thereby protecting the teeth from excessive decay and the gums from accelerated deterioration.

8 Claims, No Drawings

ULTRA HIGH-FOAM DENTIFRICE

This application is a continuation-in-part of copending application Ser. No. 176,013 filed Aug. 7, 1980, now abandoned.

BACKGROUND OF THE INVENTION

1. Field of the Invention

This invention relates to a dentifrice composition, and in particular, to one which contains at least about 25 percent soap and/or detergent which provides ultra-high viscosity (thick) foams that serve as physical scavengers of oral bacteria, food particles, and calculus whereby decay and periodontal disease are controlled and/or reduced.

2. Description of the Prior Art

Today, dentists are increasingly supportive of the belief that the two principal causes of loss of teeth are caries and periodontal disease, caries being the primary cause of tooth loss before age 35 and periodontal disease the primary cause after age 35.

Additionally, there are two special classes of bacteria that are implicated as being the major underlying factors that cause tooth decay:

(a) *Lactobacillus acidophilus* and other Lactobacilli that produce enamel-destroying lactic acid from sugars; lactic acid being the strongest acid formed by the fermentation of sugars; and, (b) Streptococci, especially *Streptococcus mutans*, having a number of properties that make it especially virulent as a promoter of tooth decay. The bacteria produce the enzyme lactic acid dehydrogenase which converts pyruvic acid (a product of the breakdown of sucrose) to lactic acid. In turn, lactic acid demineralizes tooth enamel. It produces more acid than do other Streptococci. These bacteria can survive in a low-pH environment.

In the battle against tooth decay, many antiseptics have been used, such as castor oil soap, detergents (cationic, nonionic, anionic), chlorhexidine, cholesterin, alexidine, and iodine.

More specifically, U.S. Pat. No. 1,484,415 provides the use of 1.5 percent iodine as an antiseptic substance in a dentrifice. U.S. Pat. No. 3,989,813 teaches the use of 1,6-di (p-chlorophenyl diguanidohexane) as an antidecay agent in a dentifrice, an agent which inhibits the growth of many microorganisms such as *Lactobacillus acidophilus odontolyticus*. U.S. Pat. No. 4,206,198 discloses a dentifrice containing a cationic antidecay agent plus a nonionic surfactant to promote foaming.

In U.S. Pat. No. 2,773,801, less than 5 percent of a foaming detergent based on a derivative of coconut oil is described as one ingredient of many in a dental cream.

Soaps have been used in dentrifices, up to concentrations of about 15 percent maximum.

U.S. Pat. No. 1,379,744 discloses a composition comprising essentially of a combination of chalk, sulfur, common salt, and soap, all conveniently and preferably mixed together in powder form, with the composition containing soap in an amount up to 12.5 percent.

In addition, U.S. Pat. No. 2,027,535 provides the use of up to 5 percent soap.

U.S. Pat. No. 1,633,336 provides a dentrific composition containing many ingredients one of which is castor oil soap in levels of one percent.

SUMMARY OF THE INVENTION

The present invention contemplates a dentifrice comprising as essential ingredients a non-toxic soap and/or detergent without an unpleasant taste at concentrations from at least about 25 percent to about 50 percent and water, the dentifrice having a minimum alkaline pH of 7.5, being capable of producing high viscosity bodied foams capable of physically capturing mouth bacteria and food particles, and allowing these foreign substances to be flushed away with the foam thereby protecting the teeth from excessive decay and the gums from accelerated deterioration.

DESCRIPTION OF THE PREFERRED EMBODIMENTS

There is made in accordance with the invention a dental cream which contains as its essential non-aqueous ingredient preferably a non-toxic soap, such as a soap made from a combination of animal tallows and coconut oil, in concentrations never before used as a dentifrice; namely at least about 25 percent to about 50 percent, based upon the weight of the dentifrice, emulsified in water. This invention is based upon the discovery that foams produced from very high solid soaps in water contain firm hollow globes (bubbles) capable of entrapping and physically holding bacteria, food particles, and debris from their lodgings on the surfaces of the teeth, as well as the free areas of the gingiva adjacent to the teeth and the cementum. Following brushing, the foam is flushed from the mouth carrying with it the entrapped substances.

Such high-bodied foams because of their high concentrations of soap possess an alkaline pH not lower than about 7.5. At this pH mouth acids are instantly neutralized and the alkaline pH serves as a stimulant of the gum tissues. Preferably, the soaps are sodium soaps and commercially available Ivory and Castile soaps are satisfactory. The viscosity of foams increases as the concentration of the soap is increased. As the concentration exceeds about 25 percent, there is a dramatic increase in viscosity as the concentration is increased. Also the nature of the foam also varies substantially. The foam produced by a 15 percent soap solution at room temperature (22° C.) may be poured from a container. When such foam is heated to about body temperature (37° C.), the foam begins to break down and becomes watery. On the other hand, when the concentration increases to about 25 percent, the foam at room temperature is of substantially higher viscosity, is non-pourable, stable, and has the appearance of heavy whipped cream. As the temperature is increased to body temperature, there is a slight increase in viscosity. As the concentration of the soap is increased, the viscosity increases at both room and body temperatures and the foams have the appearance of heavy whipped cream, are non-pourable, and are stable.

The relationship between the soap concentration and viscosity of the foams at both room temperature and body temperature is shown in Table I. The soap used for the observations was commercial Ivory soap.

TABLE I

| Soap | Viscosity, 22° C. | Viscosity, 37° C. |
|---|---|---|
| 15% | 3,500 cps | 1,250 cps |
| 25% | 10,000 cps | 11,750 cps |
| 33.5% | 30,000 cps | 18,000 cps |

Although the maximum concentration of soap in prior art dentifrices is about 12.5 percent, the minimum concentration used in the above determinations was 15 percent. As stated above, foams at concentrations of at least about 25 percent are stable at both room and body temperatures and resemble heavy whipped cream. As the concentration of soap exceeds about 50 percent, the composition does not produce the high viscosity foams but produces a discontinuous granular structure resembling and having the consistency of cottage cheese. Such structure does not have the capability of entrapping and holding the desired high proportion of foreign substances although it will remove some foreign material.

The dentifrices of this invention are highly effective in removing foreign substances and are more effective as a bacteriostat than a commercial, highly advertised toothpaste and other commonly recommended substances for the cleaning of teeth.

Various other ingredients other than the essential high concentrations of an alkaline soap may be incorporated in the oral preparations of this invention. Examples of such ingredients include coloring or whitening agents, preservatives, solubilizing or compatibilizing agents, silicones, chlorophyll compounds and ammoniated material as urea, diammonium phosphate, and mixtures thereof. These adjuvants, where present, are incorporated in the preparations in amounts which do not substantially adversely affect the properties and characteristics desired, particularly the high viscosity foaming ability.

Any suitable flavoring or sweetening materials may also be employed. Examples of suitable flavoring constituents are flavoring oils, e.g., oils of spearmint, peppermint, wintergreen, sassafras, clove, sage, eucalyptus, marjoram, cinnamon, lemon and orange, and sodium methylsalicylate. Suitable sweetening agents include sucrose, lactose, maltose, sorbitol, sodium cyclamate, perillartine and saccharin. Suitably, the flavor and sweetening agents may together comprise from 0.01 percent to 5 percent or more of the preparation.

The invention is illustrated by the following specific examples, in which parts are by weight.

EXAMPLE 1

A dental cream was made which contains:

| Ingredient | Part By Wt |
| --- | --- |
| Conventional Fatty Acid Soap Made from Beef and Pork Tallow and Coconut Oil | 40.0 |
| Sweetener | 0.20 |
| Sodium Benzoate | 0.50 |
| Oil of Cloves | 0.80 |
| Glycerin | 1.50 |
| Water | 53.0 |

The resulting dentifrice produced a very heavy-bodied astringent foam when used with a regular or electric toothbrush, a foam resembling whipped cream, which sweeps up and physically holds mouth bacteria, food particles, and gum line debris that are subsequently flushed out of the mouth with water. Evidence of such entrapments can be readily observed by microscopic inspection.

EXAMPLE 2

A dentifrice was made which contains:

| Ingredient | Part By Wt |
| --- | --- |
| Ultra Pure Castile Soap | 35.0 |
| Ethanol | 3.0 |
| Glycerin | 3.0 |
| Polishing Agent ($Ca_3(PO_4)_2.2H_2O$) | 10.0 |
| Sweetener | 0.50 |
| Preservative | 0.50 |
| Peppermint Oil | 0.30 |
| Anise Oil | 0.20 |
| Water | 57.5 |

The resulting dentifrice produced a very heavy-bodied astringent foam when used with a regular or electric toothbrush, a foam resembling whipped cream, which sweeps up and physically holds mouth bacteria, food particles, and gum line debris that are subsequently flushed out of the mouth with water. Evidence of such entrapments can be readily observed by microscopic inspection.

EXAMPLE 3

A dental cream was made which contains:

| Ingredient | Part By Wt |
| --- | --- |
| Soaps (e.g. ultra pure soap based on animal tallow and coconut oil) | 42.5 |
| Mouthwash Formula (in lieu of water) - any conventional commercial mouthwash | 57.5 |

The resulting dentifrice produced a very heavy-bodied astringent foam when used with a regular or electric toothbrush, a foam resembling whipped cream, which sweeps up and physically holds mouth bacteria, food particles, and gum line debris that are subsequently flushed out of the mouth with water. Evidence of such entrapments can be readily observed by microscopic inspection.

What is claimed is:

1. In the art of cleaning teeth with a regular or electric toothbrush the improvement which consists essentially of the step of using the toothbrush with a heavy-bodied astringent dentifrice resembling, in texture, whipped cream, which sweeps up and physically holds, or which entraps mouth bacteria, food particles and gum line debris which can be subsequently flushed out of the mouth with water, the dentifrice comprising essentially water and a non-toxic, alkaline soap, the soap constituting at least about 25 percent up to about 50 percent of the weight of the dentifrice and being further characterized in producing a high viscosity, stable foam having a pH of at least about 7.5, the foam consisting of a multiplicity of firm, discrete bubbles which entrap and physically hold and, upon flushing with water, carry away mouth bacteria, food particles and gum line debris on and adjacent the surfaces of and crevices between the teeth.

2. The method of claim 1 utilizing with said toothbrush a dentifrice as defined in claim 1 which includes minor proportions of at least one of coloring or whitening agents, preservatives, sweeteners, flavoring constituents and abrasives.

3. The method of claim 1 utilizing with said toothbrush a dentifrice as defined in claim 1 wherein the soap is a sodium soap prepared from animal tallows and coconut oil.

4. The method of claim 1 utilizing with said toothbrush a dentifrice as defined in claim 1 which includes minor proportions of at least one of coloring or whitening agents, preservatives, sweeteners, flavoring constituents and abrasives and the soap is a sodium soap prepared from animal tallows and coconut oil.

5. The method of claim 1 utilizing with said toothbrush a dentifrice as defined in claim 1 wherein the soap is an ultra pure soap.

6. The method of claim 1 utilizing with said toothbrush a dentifrice as defined in claim 1 which includes minor proportions of at least one of coloring or whitening agents, preservatives, sweeteners, flavoring constituents and abrasives and the soap is an ultra pure soap.

7. The method of claim 1 utilizing with said toothbrush a dentifrice as defined in claim 1 wherein the soap is Castile soap.

8. The method of claim 1 utilizing with said toothbrush a dentifrice as defined in claim 1 which includes minor proportions of at least one of coloring or whitening agents, preservatives, sweeteners, flavoring constituents and abrasives and the soap is Castile soap.

* * * * *